(12) United States Patent
Zelenchuk

(10) Patent No.: US 7,310,547 B2
(45) Date of Patent: *Dec. 18, 2007

(54) FLUORESCENT FIBEROPTIC PROBE FOR TISSUE HEALTH DISCRIMINATION

(75) Inventor: Alex R. Zelenchuk, Stoughton, MA (US)

(73) Assignee: Medispectra, Inc., Lexington, MA (US)

( * ) Notice: Subject to any disclaimer, the term of this patent is extended or adjusted under 35 U.S.C. 154(b) by 405 days.

This patent is subject to a terminal disclaimer.

(21) Appl. No.: 10/894,356

(22) Filed: Jul. 19, 2004

(65) Prior Publication Data

US 2005/0043635 A1    Feb. 24, 2005

Related U.S. Application Data

(63) Continuation of application No. 10/192,836, filed on Jul. 10, 2002, now Pat. No. 6,768,918.

(51) Int. Cl.
*A61B 6/00* (2006.01)

(52) U.S. Cl. .................. 600/407; 600/477; 600/478

(58) Field of Classification Search .......... 600/407, 600/473, 475–478; 436/63, 64, 172
See application file for complete search history.

(56) References Cited

U.S. PATENT DOCUMENTS

| 3,013,467 | A | 12/1961 | Minsky ............................ 88/14 |
| 3,632,865 | A | 1/1972 | Haskell et al. ................... 178/6 |
| 3,809,072 | A | 5/1974 | Ersek et al. ..................... 128/23 |
| 3,890,462 | A | 6/1975 | Limb et al. ..................... 178/6.8 |
| 3,963,019 | A | 6/1976 | Quandt et al. ................... 128/2 |
| D242,393 | S | 11/1976 | Bauman ....................... D24/138 |
| D242,396 | S | 11/1976 | Bauman ....................... D24/138 |
| D242,397 | S | 11/1976 | Bauman ....................... D24/138 |
| D242,398 | S | 11/1976 | Bauman ....................... D24/138 |
| 4,017,192 | A | 4/1977 | Rosenthal et al. ........... 356/201 |
| 4,071,020 | A | 1/1978 | Puglise et al. ................... 128/2 |
| 4,198,571 | A | 4/1980 | Sheppard ....................... 250/571 |

(Continued)

FOREIGN PATENT DOCUMENTS

EP         0 135 134         3/1985

(Continued)

OTHER PUBLICATIONS

European Search Report for Pending European Patent Application No. 02019837-0, Jan. 14, 2004 (4 pgs.).

(Continued)

*Primary Examiner*—Ruth S. Smith
(74) *Attorney, Agent, or Firm*—Fish & Richardson P.C.

(57) ABSTRACT

A system and method for the in situ discrimination of healthy and diseased tissue. A fiberoptic based probe is employed to direct ultraviolet illumination onto a tissue specimen and to collect the fluorescent response radiation. The response radiation is observed at three selected wavelengths, one of which corresponds to an isosbestic point. In one example, the isosbestic point occurs at about 431 nm. The intensities of the observed signals are normalized using the 431 nm intensity. A score is determined using the ratios in a discriminant analysis. The tissue under examination is resected or not, based on the diagnosis of disease or health, according to the outcome of the discriminant analysis.

11 Claims, 4 Drawing Sheets

U.S. PATENT DOCUMENTS

| | | | |
|---|---|---|---|
| 4,218,703 A | 8/1980 | Netravali et al. | 358/136 |
| 4,254,421 A | 3/1981 | Kreutel, Jr. | 343/754 |
| 4,273,110 A | 6/1981 | Groux | 128/6 |
| 4,349,510 A | 9/1982 | Kolehmainen et al. | |
| 4,357,075 A | 11/1982 | Hunter | 350/294 |
| 4,396,579 A | 8/1983 | Schroeder et al. | |
| 4,397,557 A | 8/1983 | Herwig et al. | 356/342 |
| 4,515,165 A | 5/1985 | Carroll | |
| 4,549,229 A | 10/1985 | Nakano et al. | 360/8 |
| 4,558,462 A | 12/1985 | Horiba et al. | |
| 4,641,352 A | 2/1987 | Fenster et al. | |
| 4,646,722 A | 3/1987 | Silverstein et al. | 128/4 |
| 4,662,360 A | 5/1987 | O'Hara et al. | 128/9 |
| 4,733,063 A | 3/1988 | Kimura et al. | 250/201 |
| 4,741,326 A | 5/1988 | Sidall et al. | 128/4 |
| 4,753,530 A | 6/1988 | Knight et al. | 356/73 |
| 4,755,055 A | 7/1988 | Johnson et al. | |
| 4,768,513 A | 9/1988 | Suzuki | 128/634 |
| 4,800,571 A | 1/1989 | Konishi | 375/10 |
| 4,803,049 A | 2/1989 | Hirschfeld et al. | |
| 4,844,617 A | 7/1989 | Kelderman et al. | 356/372 |
| 4,845,352 A | 7/1989 | Benschop | 250/201 |
| 4,852,955 A | 8/1989 | Doyle et al. | 350/1.2 |
| 4,877,033 A | 10/1989 | Seitz, Jr. | 128/660.05 |
| 4,878,485 A | 11/1989 | Adair | 128/6 |
| 4,891,829 A | 1/1990 | Deckman et al. | 378/4 |
| 4,930,516 A | 6/1990 | Alfano et al. | 128/665 |
| 4,945,478 A | 7/1990 | Merickel et al. | 364/413.22 |
| 4,965,441 A | 10/1990 | Picard | 250/201.3 |
| 4,972,258 A | 11/1990 | Wolf et al. | 358/93 |
| 4,974,580 A | 12/1990 | Anapliotis | 128/4 |
| 4,979,498 A | 12/1990 | Oneda et al. | 128/6 |
| 4,997,242 A | 3/1991 | Amos | 350/6.91 |
| 5,003,979 A | 4/1991 | Merickel et al. | 364/413.22 |
| 5,011,243 A | 4/1991 | Doyle et al. | 350/1.2 |
| 5,022,757 A | 6/1991 | Modell | 356/318 |
| 5,028,802 A | 7/1991 | Webb et al. | 250/571 |
| 5,032,720 A | 7/1991 | White | 250/236 |
| 5,034,613 A | 7/1991 | Denk et al. | 250/458.1 |
| 5,036,853 A | 8/1991 | Jeffcoat et al. | 128/634 |
| 5,042,494 A | 8/1991 | Alfano | 128/665 |
| 5,048,946 A | 9/1991 | Sklar et al. | 351/206 |
| 5,054,926 A | 10/1991 | Dabbs et al. | 356/345 |
| 5,065,008 A | 11/1991 | Hakamata et al. | 250/216 |
| 5,071,246 A | 12/1991 | Blaha et al. | 351/221 |
| 5,074,306 A | 12/1991 | Green et al. | 128/664 |
| 5,083,220 A | 1/1992 | Hill | 359/234 |
| 5,091,652 A | 2/1992 | Mathies et al. | 250/458.1 |
| 5,101,825 A | 4/1992 | Gravenstein et al. | 600/326 |
| 5,120,953 A | 6/1992 | Harris | 250/227.2 |
| 5,122,653 A | 6/1992 | Ohki | 250/216 |
| 5,131,398 A * | 7/1992 | Alfano et al. | 600/476 |
| 5,132,526 A | 7/1992 | Iwasaki | 250/201.3 |
| 5,139,025 A | 8/1992 | Lewis et al. | 128/665 |
| 5,154,166 A | 10/1992 | Chikama | 128/4 |
| 5,159,919 A | 11/1992 | Chikama | 128/4 |
| 5,161,053 A | 11/1992 | Dabbs | 359/384 |
| 5,162,641 A | 11/1992 | Fountain | 250/201.2 |
| 5,162,941 A | 11/1992 | Favro et al. | 359/386 |
| 5,168,157 A | 12/1992 | Kimura | 250/234 |
| 5,192,980 A | 3/1993 | Dixon et al. | 356/326 |
| 5,193,525 A | 3/1993 | Silverstein et al. | 128/4 |
| RE34,214 E | 4/1993 | Carlsson et al. | 358/93 |
| 5,199,431 A | 4/1993 | Kittrell et al. | 128/634 |
| 5,201,318 A | 4/1993 | Rava et al. | 128/665 |
| 5,201,908 A | 4/1993 | Jones | 128/4 |
| 5,203,328 A | 4/1993 | Samuels et al. | 128/633 |
| 5,205,291 A | 4/1993 | Potter | |
| 5,225,671 A | 7/1993 | Fukuyama | 250/216 |
| 5,235,457 A | 8/1993 | Lichtman et al. | 359/368 |
| 5,237,984 A | 8/1993 | Williams, III et al. | 128/4 |
| 5,239,178 A | 8/1993 | Derndinger et al. | 250/234 |
| 5,248,876 A | 9/1993 | Kerstens et al. | 250/561 |
| 5,253,071 A | 10/1993 | MacKay | 358/222 |
| 5,257,617 A | 11/1993 | Takahashi | 128/4 |
| 5,260,569 A | 11/1993 | Kimura | 250/234 |
| 5,260,578 A | 11/1993 | Bliton et al. | 250/461.1 |
| 5,261,410 A | 11/1993 | Alfano et al. | 128/664 |
| 5,262,646 A | 11/1993 | Booker et al. | 250/341 |
| 5,267,179 A | 11/1993 | Butler et al. | |
| 5,274,240 A | 12/1993 | Mathies et al. | 250/458.1 |
| 5,284,149 A | 2/1994 | Dhadwal et al. | 128/665 |
| 5,286,964 A | 2/1994 | Fountain | 250/201.2 |
| 5,289,274 A | 2/1994 | Kondo | 348/208 |
| 5,294,799 A | 3/1994 | Aslund et al. | 250/458.1 |
| 5,296,700 A | 3/1994 | Kumagai | 250/216 |
| 5,303,026 A | 4/1994 | Strobl et al. | 356/318 |
| 5,306,902 A | 4/1994 | Goodman | 250/201.3 |
| 5,313,567 A | 5/1994 | Civanlar et al. | 395/124 |
| 5,319,200 A | 6/1994 | Rosenthal et al. | 250/341 |
| 5,321,501 A | 6/1994 | Swanson et al. | 356/345 |
| 5,324,979 A | 6/1994 | Rosenthal | 250/504 R |
| 5,325,846 A | 7/1994 | Szabo | 128/4 |
| 5,329,352 A | 7/1994 | Jacobsen | 356/301 |
| 5,337,734 A | 8/1994 | Saab | 128/4 |
| 5,343,038 A | 8/1994 | Nishiwaki et al. | 250/234 |
| 5,345,306 A | 9/1994 | Ichimura et al. | 356/346 |
| 5,345,941 A | 9/1994 | Rava et al. | 128/665 |
| 5,349,961 A | 9/1994 | Stoddart et al. | 128/665 |
| 5,383,874 A | 1/1995 | Jackson et al. | |
| 5,398,685 A | 3/1995 | Wilk et al. | 128/653.1 |
| 5,402,768 A | 4/1995 | Adair | 128/4 |
| 5,406,939 A | 4/1995 | Bala | 128/4 |
| 5,412,563 A | 5/1995 | Cline et al. | |
| 5,413,092 A | 5/1995 | Williams, III et al. | 128/4 |
| 5,413,108 A | 5/1995 | Alfano | 128/665 |
| 5,415,157 A | 5/1995 | Welcome | 128/4 |
| 5,418,797 A | 5/1995 | Bashkansky et al. | 372/3 |
| 5,419,311 A | 5/1995 | Yabe et al. | 128/4 |
| 5,419,323 A | 5/1995 | Kittrell et al. | 128/653 |
| 5,421,337 A | 6/1995 | Richards-Kortum et al. | 128/665 |
| 5,421,339 A | 6/1995 | Ramanujam et al. | 128/665 |
| 5,424,543 A | 6/1995 | Dombrowski et al. | 250/330 |
| 5,450,857 A | 9/1995 | Garfield et al. | 128/778 |
| 5,451,931 A | 9/1995 | Miller et al. | 340/630 |
| 5,452,723 A | 9/1995 | Wu et al. | |
| 5,458,132 A | 10/1995 | Yabe et al. | 128/4 |
| 5,458,133 A | 10/1995 | Yabe et al. | 600/121 |
| 5,467,767 A | 11/1995 | Alfano et al. | 128/665 |
| 5,469,853 A | 11/1995 | Law et al. | 128/662.06 |
| 5,477,382 A | 12/1995 | Pernick | 359/559 |
| 5,480,775 A | 1/1996 | Ito et al. | 435/7.2 |
| 5,493,444 A | 2/1996 | Khoury et al. | 359/559 |
| 5,496,259 A | 3/1996 | Perkins | 600/124 |
| 5,507,295 A | 4/1996 | Skidmore | 600/121 |
| 5,516,010 A | 5/1996 | O'Hara et al. | 600/122 |
| 5,519,545 A | 5/1996 | Kawahara | 360/46 |
| 5,529,235 A | 6/1996 | Bolarski et al. | 227/175.1 |
| 5,536,236 A | 7/1996 | Yabe et al. | 600/125 |
| 5,545,121 A | 8/1996 | Yabe et al. | 600/121 |
| 5,551,945 A | 9/1996 | Yabe et al. | 600/122 |
| 5,556,367 A | 9/1996 | Yabe et al. | 600/124 |
| 5,562,100 A | 10/1996 | Kittrell et al. | 128/665 |
| 5,579,773 A | 12/1996 | Vo-Dinh et al. | 128/665 |
| 5,582,168 A | 12/1996 | Samuels et al. | 128/633 |
| 5,587,832 A | 12/1996 | Krause | 359/385 |
| 5,596,992 A | 1/1997 | Haaland et al. | 128/664 |
| 5,599,717 A | 2/1997 | Vo-Dinh | 436/63 |
| 5,609,560 A | 3/1997 | Ichikawa et al. | 600/101 |
| 5,612,540 A | 3/1997 | Richards-Kortum et al. | 250/461.2 |
| 5,623,932 A | 4/1997 | Ramanujam et al. | 128/665 |
| 5,643,175 A | 7/1997 | Adair | |

| Patent No. | Date | Inventor | Class |
|---|---|---|---|
| 5,647,368 A | 7/1997 | Zeng et al. | 128/665 |
| 5,659,384 A | 8/1997 | Ina | |
| 5,662,588 A | 9/1997 | Lida | 600/121 |
| 5,685,822 A | 11/1997 | Harhen | 600/125 |
| 5,690,106 A | 11/1997 | Bani-Hashemi et al. | 128/653.1 |
| 5,693,043 A | 12/1997 | Kittrell et al. | 606/15 |
| 5,695,448 A | 12/1997 | Kimura et al. | 600/121 |
| 5,697,373 A | 12/1997 | Richards-Kortum et al. | 128/664 |
| 5,699,795 A | 12/1997 | Richards-Kortum | 128/634 |
| 5,704,892 A | 1/1998 | Adair | 600/121 |
| 5,707,343 A | 1/1998 | O'Hara et al. | 600/121 |
| 5,713,364 A | 2/1998 | DeBarsyhe et al. | 128/664 |
| 5,717,209 A | 2/1998 | Bigman et al. | 250/339.12 |
| 5,720,293 A | 2/1998 | Quinn et al. | |
| 5,730,701 A | 3/1998 | Furukawa et al. | 600/127 |
| 5,733,244 A | 3/1998 | Yasui et al. | 600/127 |
| 5,735,276 A | 4/1998 | Lemelson | 128/653 |
| 5,746,695 A | 5/1998 | Yasui et al. | 600/127 |
| 5,768,333 A | 6/1998 | Abdel-Mottaleb | 378/37 |
| 5,769,792 A | 6/1998 | Palcic et al. | 600/477 |
| 5,773,835 A | 6/1998 | Sinofsky et al. | 250/462.1 |
| 5,784,162 A | 7/1998 | Cabib et al. | |
| 5,791,346 A | 8/1998 | Craine et al. | 128/653 |
| 5,795,632 A | 8/1998 | Buchalter | 428/35.2 |
| 5,800,350 A | 9/1998 | Coppleson et al. | 600/372 |
| 5,807,248 A | 9/1998 | Mills | 600/322 |
| 5,813,987 A | 9/1998 | Modell et al. | 600/473 |
| 5,817,015 A | 10/1998 | Adair | 600/121 |
| 5,830,146 A | 11/1998 | Skladnev et al. | 600/478 |
| 5,833,617 A | 11/1998 | Hayashi | 600/476 |
| 5,838,435 A | 11/1998 | Sandison | |
| 5,840,035 A | 11/1998 | Heusmann et al. | 600/47 |
| 5,842,995 A | 12/1998 | Mahadevan-Jansen et al. | 600/473 |
| 5,855,551 A | 1/1999 | Sklandev et al. | 600/372 |
| 5,860,913 A | 1/1999 | Yamaya et al. | 600/476 |
| 5,863,287 A | 1/1999 | Segawa | 600/121 |
| 5,865,726 A | 2/1999 | Katsurada et al. | 600/127 |
| 5,871,439 A | 2/1999 | Takahashi et al. | |
| 5,876,329 A | 3/1999 | Harhen | 600/125 |
| 5,894,340 A | 4/1999 | Loree et al. | |
| 5,902,246 A | 5/1999 | McHenry et al. | |
| 5,912,257 A | 6/1999 | Prasad et al. | |
| 5,920,399 A | 7/1999 | Sandison et al. | 356/418 |
| 5,921,926 A | 7/1999 | Rolland et al. | 600/407 |
| 5,929,985 A | 7/1999 | Sandison et al. | 365/318 |
| 5,931,779 A | 8/1999 | Arakaki et al. | 600/310 |
| 5,938,617 A | 8/1999 | Vo-Dinh | 600/476 |
| 5,941,834 A | 8/1999 | Skladnev et al. | 600/587 |
| 5,983,125 A | 11/1999 | Alfano et al. | 600/473 |
| 5,987,343 A | 11/1999 | Kinast | |
| 5,989,184 A | 11/1999 | Blair et al. | 600/167 |
| 5,991,653 A | 11/1999 | Richards-Kortum et al. | 660/475 |
| 5,995,645 A | 11/1999 | Soenksen et al. | 382/133 |
| 5,999,844 A | 12/1999 | Gombrich et al. | |
| 6,011,596 A | 1/2000 | Burl et al. | |
| 6,021,344 A | 2/2000 | Lui et al. | |
| 6,026,319 A | 2/2000 | Hayashi | |
| 6,058,322 A | 5/2000 | Nishikawa et al. | 600/408 |
| 6,067,371 A | 5/2000 | Gouge et al. | |
| 6,069,689 A | 5/2000 | Zeng et al. | 356/773 |
| 6,083,487 A | 7/2000 | Biel | |
| 6,091,985 A | 7/2000 | Alfano et al. | 600/476 |
| 6,095,982 A | 8/2000 | Richards-Kortum et al. | 600/476 |
| 6,096,065 A | 8/2000 | Crowley | 607/88 |
| 6,099,464 A | 8/2000 | Shimizu et al. | 600/104 |
| 6,104,945 A | 8/2000 | Modell et al. | 600/473 |
| 6,119,031 A | 9/2000 | Crowley | 600/407 |
| 6,123,454 A | 9/2000 | Canfield et al. | |
| 6,124,597 A | 9/2000 | Shehada et al. | 250/461.2 |
| 6,135,965 A | 10/2000 | Tumor et al. | |
| 6,146,897 A | 11/2000 | Cohenford et al. | 436/63 |
| 6,166,079 A | 12/2000 | Follen et al. | |
| 6,169,817 B1 | 1/2001 | Parker et al. | 382/131 |
| 6,187,289 B1 | 2/2001 | Richards-Kortum et al. | |
| 6,208,887 B1 | 3/2001 | Clarke et al. | 600/476 |
| 6,210,331 B1 | 4/2001 | Raz | |
| 6,224,256 B1 | 5/2001 | Bala | |
| 6,241,662 B1 | 6/2001 | Richards-Kortum et al. | 600/310 |
| 6,243,601 B1 | 6/2001 | Wist | 600/477 |
| 6,246,471 B1 | 6/2001 | Jung et al. | 356/73 |
| 6,246,479 B1 | 6/2001 | Jung et al. | 356/419 |
| 6,258,576 B1 | 7/2001 | Richars-Kortum et al. | |
| 6,277,067 B1 | 8/2001 | Blair | |
| 6,285,639 B1 | 9/2001 | Maenza et al. | 369/47.28 |
| 6,312,385 B1 | 11/2001 | Mo et al. | 600/443 |
| 6,317,617 B1 | 11/2001 | Gilhuijs et al. | 600/408 |
| 6,332,092 B1 | 12/2001 | Deckert et al. | |
| D453,832 S | 2/2002 | Morrell et al. | D24/138 |
| D453,962 S | 2/2002 | Morrell et al. | D24/138 |
| D453,963 S | 2/2002 | Morrell et al. | D24/138 |
| D453,964 S | 2/2002 | Morrell et al. | D24/138 |
| 6,370,422 B1 | 4/2002 | Richards-Kortum et al. | |
| 6,373,998 B2 | 4/2002 | Thirion et al. | |
| 6,377,842 B1 | 4/2002 | Pogue et al. | 600/478 |
| 6,385,484 B2 | 5/2002 | Nordstrom et al. | 600/476 |
| 6,390,671 B1 | 5/2002 | Tseng | |
| 6,405,070 B1 | 6/2002 | Banerjee | |
| 6,411,835 B1 | 6/2002 | Modell et al. | 600/407 |
| 6,411,838 B1 | 6/2002 | Nordstrom et al. | 600/476 |
| D460,821 S | 7/2002 | Morrell et al. | D24/138 |
| 6,421,553 B1 | 7/2002 | Costa et al. | 600/476 |
| 6,424,852 B1 | 7/2002 | Zavislan | |
| 6,427,082 B1 | 7/2002 | Nordstrom et al. | 600/476 |
| 6,466,687 B1 | 10/2002 | Uppaluri et al. | |
| 6,487,440 B2 | 11/2002 | Deckert et al. | |
| 6,497,659 B1 | 12/2002 | Rafert | |
| 6,571,118 B1 | 5/2003 | Utzinger et al. | 600/476 |
| 6,574,502 B2 | 6/2003 | Hayashi | 600/476 |
| 6,593,101 B2 | 7/2003 | Richards-Kortum et al. | |
| 6,593,102 B2 | 7/2003 | Zahniser | |
| 6,639,674 B2 | 10/2003 | Sokolov et al. | |
| 6,697,666 B1 | 2/2004 | Richards-Kortum et al. | |
| 6,760,613 B2 | 7/2004 | Nordstrom et al. | |
| 6,766,184 B2 | 7/2004 | Utzinger et al. | |
| 6,768,918 B2 | 7/2004 | Zelenchuk | |
| 6,818,903 B2 | 11/2004 | Schomacker et al. | |
| 6,826,422 B1 | 11/2004 | Modell et al. | |
| D500,134 S | 12/2004 | Banks et al. | |
| 6,839,661 B2 | 1/2005 | Costa et al. | |
| 6,847,490 B1 | 1/2005 | Nordstrom et al. | |
| 6,902,935 B2 | 6/2005 | Kaufman et al. | |
| D507,349 S | 7/2005 | Banks et al. | |
| 6,933,154 B2 | 8/2005 | Schomacker et al. | |
| 7,015,310 B2 * | 3/2006 | Remington et al. | 530/350 |
| 2001/0041843 A1 | 11/2001 | Modell et al. | |
| 2002/0007122 A1 | 1/2002 | Kaufman et al. | |
| 2002/0007123 A1 | 1/2002 | Balas et al. | |
| 2002/0107668 A1 | 8/2002 | Costa et al. | |
| 2002/0127735 A1 | 9/2002 | Kaufman et al. | |
| 2002/0133073 A1 | 9/2002 | Nordstrom et al. | |
| 2002/0177777 A1 | 11/2002 | Nordstrom et al. | |
| 2002/0183626 A1 | 12/2002 | Nordstrom et al. | |
| 2002/0197728 A1 | 12/2002 | Kaufman et al. | |
| 2003/0095721 A1 | 5/2003 | Clume et al. | |
| 2003/0114762 A1 | 6/2003 | Balas | |
| 2003/0144585 A1 | 7/2003 | Kaufman et al. | |
| 2003/0163049 A1 | 8/2003 | Balas | |
| 2003/0207250 A1 | 11/2003 | Kaufman et al. | |
| 2004/0007674 A1 | 1/2004 | Schomacker et al. | |
| 2004/0010187 A1 | 1/2004 | Schomacker et al. | |
| 2004/0010195 A1 | 1/2004 | Zelenchuk | |

| | | | |
|---|---|---|---|
| 2004/0010375 | A1 | 1/2004 | Schomacker et al. |
| 2004/0023406 | A1 | 2/2004 | Shomacker et al. |
| 2004/0206882 | A1 | 10/2004 | Banks et al |
| 2004/0206913 | A1 | 10/2004 | Costa et al. |
| 2004/0206914 | A1 | 10/2004 | Schomacker et al. |
| 2004/0207625 | A1 | 10/2004 | Griffin et al. |
| 2004/0208385 | A1 | 10/2004 | Jiang |
| 2004/0208390 | A1 | 10/2004 | Jiang et al. |
| 2004/0209237 | A1 | 10/2004 | Flewelling et al. |
| 2005/0054936 | A1 | 3/2005 | Balas |
| 2005/0090751 | A1 | 4/2005 | Balas |

FOREIGN PATENT DOCUMENTS

| | | |
|---|---|---|
| EP | 0 280 418 | 8/1988 |
| EP | 0 335 725 | 10/1989 |
| EP | 0 444 689 A2 | 9/1991 |
| EP | 0 474 264 | 3/1992 |
| EP | 0 641 542 | 3/1995 |
| EP | 0 689 045 A1 | 12/1995 |
| EP | 0 737 849 A2 | 10/1996 |
| SU | 1 223 092 A | 4/1986 |
| WO | WO 92/19148 | 11/1992 |
| WO | WO 93/14688 | 8/1993 |
| WO | WO 94/26168 | 11/1994 |
| WO | WO 95/00067 | 1/1995 |
| WO | WO 95/04385 | 2/1995 |
| WO | WO 97/05473 | 2/1997 |
| WO | WO 98/30889 | 2/1997 |
| WO | WO 97/48331 | 12/1997 |
| WO | WO 98/05253 | 2/1998 |
| WO | WO 98/24369 | 6/1998 |
| WO | WO 98/41176 | 9/1998 |
| WO | WO 99/18847 | 4/1999 |
| WO | WO 99/20313 | 4/1999 |
| WO | WO 99/20314 | 4/1999 |
| WO | WO 99/47041 | 9/1999 |
| WO | WO 99/57507 | 11/1999 |
| WO | WO 99/57529 | 11/1999 |
| WO | WO 00/15101 | 3/2000 |
| WO | WO 00/59366 | 10/2000 |

OTHER PUBLICATIONS

European Search Report for Pending European Patent Application No. 00938257, Jun. 14, 2005 (3 pgs.).

International Search Report for International Application No. PCT/US04/11820 dated Sep. 3, 2004 (3 pages).

Ko et al., "Multiresolution Registration of Coronary Artery Image Sequences," *International Journal of Medical Informatics*, vol. 44 (1997), pp. 93-104.

Noble et al., "Automated, Nonrigid Alignment of Clinical Myocardial Contrast Echocardiography Image Sequences: Comparison with Manual Alignment," *Ultrasound in Medicine and Biology*, vol. 28, No. 1 (2002), pp. 115-123.

Written Opinion for International Application No. PCT/US04/11820 dated September 29, 2004 (5 pages).

Balas (1997), "An Imaging Colorimeter for Noncontract Tissue Color Mapping," *IEEE Transactions on Biomedical Engineering*, 44(6):468-474.

Balas (2001), "A Novel Optical Imaging Method for the Early Detection, Quantitative Grading, and Mapping of Cancerous and Precancerous Lesions of Cervix," *IEEE Transactions on Biomedical Engineering*, 48(1):96-104.

Balas et al. (1997), "A modular diffuse reflection and fluorescence emission imaging colorimeter for the in-vivo study of parameters related with the phototoxic effect in PDT," *SPIE*, 3191:50-57.

Balas et al. (1998), "In Vivo Assessment of Acetic Acid-Cervical Tissue Interaction Using Quantitative Imaging of Back-Scattered Light: Its Potential Use for the In Vivo Cervical Cancer Detection Grading and Mapping," Part of EUROPTO Conference on Optical Biopsy, Stockholm, Sweden,*SPIE*, vol. 3568:31-37.

Balas et al. (1999), "In Vivo Detection and Staging of Epithelial Dysplasias and Malignancies Based on the Quantitative Assessment of Acetic Acid-Tissue Interaction Kinetics," *Journal of Photochemistry and Photobiology B: Biology*, 53:153-157.

Bessey et al. (1949), "The Fluorometric measurement of the nucleotides of riboflavin and their concentration in tissues," *J. Bio.-Chem.*; 180:755-769.

Bors et al. (1998), "Optical flow estimation and moving object segmentation based on median radial basis function network," *IEEE Transactions on Image Processing*, 7(5):693-702.

Bouthemy et al. (1999), "A unified approach to shot change detection and camera motion characterization," *IEEE Transactions on Circuits and Systems for Video Technology*, 9(7):1030-1044.

Braichotte et al. (1995), "Clinical Pharmacokinetic Studies of Photofrin by Fluorescence Spectroscopy in the Oral Cavity, the Esophagus, and the Bronchi," *Cancer* 75(11):2760-2778.

Brown (1990), "Chemometrics," *Anal. Chem.*, 62:84R-101R.

Camus et al. (1997), "Real-time quantized optical flow," *Real-Time Imaging*, 3:71-86.

Caplier et al. (1998), "Real-time implementation of a MRF-based motion detection algorithm," *Real-Time Imaging*, 4:41-54.

Contini et al. (1989), "Colposcopy and Computer Graphics: a New Method?" *Amer. J. Obstet. Gynecol.*, 160(3):535-538.

Craine et al., (1993), "Digital Imaging Colposcopy: basic concepts and applications," *Amer. J. Obstet. Gynecol.*, 82(5):869-873.

Craine et al. (1998), "Digital imaging colposcopy: Corrected area measurements using shape-from-shading," *IEEE Transactions on Medical Imaging*, 17(6):1003-1010.

Crisp et al. (1990), "The Computerized Digital Imaging Colposcope: Future Directions," *Amer. J. Obstet. Gynecol.*, 162(6):1491-1497.

Cronjé et al. (1997), "Effects of Dilute Acetic Acid on the Cervical Smear," *Acta. Cytol.*, 41:1091-1094.

Davidovits et al. (1971), "Scanning Laser Microscope for Biological Investigations", *Applied Optics*, 10(7):1615-1619.

Dickman et al. (2001), "Identification of Cervical Neoplasia Using a Simulation of Human Vision," *Journal of Lower Genital Tract Disease*, 5(3):144-152.

Drezek et al. (1999), "Light scattering from cells: finite-difference time-domain simulations and goniometric measurements," *Applied Optics* 38(16):3651-3661.

Drezek et al. (2000), "Laser Scanning Confocal Microscopy of Cervical Tissue Before and After Application of Acetic Acid," *Am. J. Obstet. Gynecol.*, 182(5):1135-1139.

Dumontier et al. (1999), "Real-time DSP implementation for MRF-based video motion detection," *IEEE Transactions on Image Processing*, 8(10):1341-1347.

Earnshaw et al. (1996), "The Performance of Camera Translation Direction Estimators from Optical Flow: Analysis, Comparison, and Theoretical Limits," *IEEE Transactions on Pattern Analysis and Machine Intelligence*, 18(9):927-932.

Edebiri, A.A. (1990), "The relative significance of colposcopic discriptive appearances in the dianosis of cervical intraepithelial neoplasia," *Int. J. Gynecol. Obstet.*, 33:23-29.

Eisner et al. (1987), "Use of Cross-Correlation Function to Detect Patient Motion During Spectral Imaging," *Journal of Nuclear Medicine*, 28(1):97-101.

Ferris et al. (1998), "Colposcopy Quality Control: Establishing Colposcopy Criterion Standards for the NCI ALTS Trial Using Cervigrams," *J. Lower Genital Tract Disease*, 2(4):195-203.

Fleet et al. (1995), "Recursive Filters for Optical Flow," *IEEE Transactions on Pattern Analysis and Machine Intelligence*, 17(1):61-67.

Gao et al. (1998), "A work minimization approach to image morphing," *The Visual Computer*, 14:390-400.

Gauch (1999), "Image Segmentation and Analysis Via Multiscale Gradient Watershed Hierarchies," *IEEE Transactions on Image Processing*, 8(1):69-79.

Hall et al. (1992), "Near-Infrared Spectrophotometry: A New Dimension in Clinical Chemistry", *Clin. Chem.* 38(9):1623-1631.

Haralick (1984), "Digital Step Edges from Zero Crossing of Second Directional Derivatives," *IEEE Transactions on Pattern Analysis and Machine Intelligence*, 6(1):58-68.

Haris et al. (1998), "Hybrid Image Segmentation Using Watersheds and Fast Region Merging," *IEEE Transactions on Image Processing*, 7(12):1684-1699.

Helmerhorst et al. (1987), "The accuracy of colposcopically directed biopsy in diagnosis of CIN 2/3." *Eur. J. Obstet. Gyn. Reprod. Biol.*, 24, 221-229.

Horn et al. (1981), "Determining Optical Flow," *Artificial Intelligence*, 17(1-3):185-203.

Horn et al. (1993), "Determining Optical Flow": a retrospective, *Artificial Intelligence*, 59:81-87.

Huang et al. (1979), "A fast two-dimensional median filtering algorithm," *IEEE Transactions on Acoustics, Speech, and Signal Processing*, 27(1):13-18.

Jackway (1996), "Gradient Watershed in Morphological Scale-Space," *IEEE Transactions on Image Processing*, 5(6):913-921.

Ji et al. (2000), "Texture Analysis for Classification of Cervix Lesions," *IEEE Transactions on Medical Imaging*, 19(11):1144-1149.

Kierkegaard et al. (1995), "Association between Colposcopic Findings and Histology in Cervical Lesions: The Significance of the Size of the Lesion" *Gynecologic Oncology*, 57:66-71.

Koester (1980), "Scanning Mirror Microscope with Optical Sectioning Characteristics: Applications in Ophthalmology", *Applied Optics*, 19(11):1749-1757.

Kumar et al. (1996), "Optical Flow: A Curve Evolution Approach," *IEEE Transactions on Image Processing*, 5(4):598-610.

Linde et al. (1980), An algorithm for vector quantizer design,: *IEEE Transactions on Communications*, 28(1):84-95.

MacAulay et al. (2002), "Variation of fluorescence spectroscopy during the menstrual cycle," *Optics Express*, 10(12):493-504.

MacLean A.B. (1999), "What is Acetowhite Epithelium," *Abstract Book; 10th World Congress of Cervical Pathology and Colposcopy*, Nov. 7-11, Buenos Aires, Argentina 41.

Marzetta et al. (1999), "A surprising radon transform result and its application to motion detection," *IEEE Transactions on Image Processing*, 8(8):1039-1049.

Miike et al. (1999), "Motion enhancement for preprocessing of optical flow and scientific visualization," *Pattern Recognition Letters*, 20:451-461.

Mikhail et al. (1995), "Computerized colposcopy and conservative management of cervical intraepithelial neoplasia in pregnancy," *Acta Obstet. Gynecol. Scand.*, 74:376-378.

Milanfar (1999), "Two-dimensional matched filtering for motion estimation," *IEEE Transactions on Image Processing*, 8(3):438-444.

Mitchell et al. (1998), "Colposcopy for the diagnosis of squamous intraepithelial lesions: a meta-analysis," *Obstet. Gynecol.*, 91(4):626-631.

Mycek et al. (1998), "Colonic polyp differentiation using time-resolved autofluorescence spectroscopy," *Gastrointestinal Endoscopy*, 48(4):390-394.

Nanda et al. (2000), "Accuracy of the Papanicolaou test in screening for and follow-up of cervical cytologic abnormalities: a systematic review," *Ann Intern Med.*, 132(10):810-819.

Nesi et al. (1998), "RETIMAC REalTIme Motion Analysis Chip," *IEEE Transactions on Circuits and Systems-II: Analog and Digital Signal Processing*, 45(3):361-375.

Noumeir et al. (1996), "Detection of Motion During Tomographic Acquisition by an Optical Flow Algorithm," *Computers and Biomedical Research*, 29(1):1-15.

O'Sullivan et al. (1994), "Interobserver variation in the diagnosis and grading of dyskaryosis in cervical smears: specialist cytopathologists compared with non-specialists," *J. Clin. Pathol.*, 47(6):515-518.

Ogura et al. (1995), "A cost effective motion estimation processor LSI using a smiple and efficient algorithm," *IEEE Transactions on Consumer Electronics*, 41(3):690-698.

Okatani et al. (1997), "Shape reconstruction from an endoscope image by shape from shading technique for a point light source at the projection center," *Computer Vision and Image Understanding*, 66(2):119-131.

Pan et al. (1998), "Correlation-feedback Technique in Optical Flow Determination," *IEEE Transactions on Image Processing*, 7(7):1061-1067.

Perona et al. (1990), "Scale-space and edge detection using anisotropic diffusion," *IEEE Transactions on Pattern Analysis and Machine Intelligence*, 12(7):629-639.

Pogue et al. (2001), "Analysis of Acetic Acid-Induced Whitening of High-Grade Squamous Intraepithelial Lesions," *Journal of Biomedical Optics*, 6(4):397-403.

Radjadhyaksha et al. (2000), "Confocal microscopy of excised human skin using acetic acid and crossed polarization: rapid detection of non-melanoma skin cancers," *Proceedings of SPIE*, 3907:84-88.

Rakshit et al. (1997), "Computation of Optical Flow Using Basis Functions," *IEEE Transactions on Image Processing*, 6(9):1246-1254.

Ramanujam et al. (1994) "In vivo diagnosis of cervical intraepithelial neoplasia using 337-nm-exited laser-induced fluorescence", *Pro. Natl. Acad. Sci. USA*, 91:10193-10197.

Ramanujam et al. (1994), "Fluorescence Spectroscopy; A Diagnostic Tool for Cervical Intraepithelial Neoplasia (CIN)," *Gynecologic Oncology*, 52:31-38.

Reid et al. (1985), "Genital warts and cervical cancer. VII. An improved colposcopic index for differentiating benign papillomaviral infections from high-grade CIN," *Am. J. Obstet. Gynecol.*, 153(6):611-618.

Richards-Kortum et al. (1994), "Description and Performance of a Fiber-optic Confocal Fluorescence Spectrometer," *Applied Spectroscopy*, 48(3):350-355.

Romano et al. (1997), "Spectroscopic study of human leukocytes," *Physica Medica*, 13:291-295.

Ruprecht et al. (1995), "Image warping with scattered data interpolation methods," *IEEE Computer Graphics and Applications*, 37-43.

Sakuma (1985), "Quantitative Analysis of the Whiteness of the Atypical Cervical Transformation Zone", *The Journal of Reproductive Medicine*, 30(10):773-776.

Schmid (1999), "Lesion Detection in Dermatoscopic Images Using Anisotropic Diffusion and Morphological Flooding," *Proceedings of the International Conference on Image Processing* (ICIP-99), 3:449-453.

Schmid (1999), "Segmentation and Symmetry Measure for Image Analysis: Application to Digital Dermatoscopy," *Ph.D. Thesis, Swiss Federal Institute of Technology (EPFL), Signal Processing Laboratory (LTS)*.

Schmid (1999), "Segmentation of Digitized Dermatoscopic Images by 2D Color Clustering," *IEEE Transactions on Medical Imaging*, 18(2):164-171.

Schmitt et al. (1994), "Confocal Microscopy in Turbid Media", *J. Opt. Soc. Am. A*, 11(8):2225-2235.

Schmitt et al. (1994), "Interferometric Versus Confocal Techniques for Imaging Microstructures in Turbid Biological Media", *Proc. SPIE*, 2135:1-12.

Schomacker et al. (1992), "Ultraviolet Laser-Induced Fluorescence of Colonic Polyps," *Gastroenterology*, 102:1155-1160.

Schomacker et al. (1992), "Ultraviolet Laser-Induced Fluorescence of Colonic Tissue; Basic Biology and Diagnostic Potential", *Lasers in Surgery and Medicine*, 12:63-78.

Schwartz (1993), "Real-time laser-scanning Confocal ratio imaging", *American Laboratory*, pp. 53-62.

Shafarenko et al. (1997), "Automatic Watershed Segmentation of Randomly Textured Color Images," *IEEE Transactions on Image Processing*, 6(11):1530-1544.

Shafi et al. (1995), "Modern image capture and data collection technology," *Clin. Obstet. Gynecol.*, 38(3):640-643.

Sheppard et al. (1978), "Depth of Field in the Scanning Microscope", *Optics Letters*, 3(3):115-117.

Szarewski et al., (1996), "Effect of smoking cessation on cervical lesions size," *Lancet*, 347:941-943.

Szeliski et al. (1997), "Spline-based image registration," *International Journal of Computer Vision*, 22(3):199-218.

Tadrous (2000), "Methods for Imaging the Structure and Function of Living Tissues and Cells: 2. Fluorescence Lifetime Imaging," *J. of Path.*, 191(3):229-234.

Thirion et al. (1999), "Deformation analysis to detect and quantify active lesions in three-dimensional medical image sequences," *IEEE Transactions on Medial Imaging*, 18(5):429-441.

Toglia et al. (1997), "Evaluation of colposcopic skills in an obstetrics and gynecology residency training program," *J. Lower Gen. Tract. Dis.*, 1(1):5-8.

Treameau et al. (1997), "A Region Growing and Merging Algorithm to Color Segmentation," *Pattern Recognition*, 30(7):1191-1203.

Van den Elsen et al. (1995), "Automatic registration of ct and mr brain images using correlation of geometrical features," *IEEE Transactions on medical imaging*, 14(2):384-396.

Vernon (1999), "Computation of Instantaneous Optical Flow Using the Phase of Fourier Components," *Image and Vision Computing*, 17:189-199.

Vincent et al. (1991), "Watersheds in Digital Spaces: An Efficient Algorithm Based on Immersion Simulations," *IEEE Transactions on Patterns Analysis and Machine Intelligence*, 13(6):583-598.

Vincent et al. (1993), "Morphological grayscale reconstruction in image analysis: Applications and efficient algorithms," *IEEE Transactions on Image Processing*, 2(2):176-201.

Wang et al. (1999), "Fast algorithms for the estimation of motion vectors," *IEEE Transactions on Image Processing*, 8(3):435-438.

Weng et al. (1997), "Three-Dimensional Surface Reconstruction Using Optical Flow for Medical Imaging," *IEEE Transactions on Medical Imaging*, 16(5):630-641.

Wolberg et al. (1998), "Image morphing: a survey," *The Visual Computer*, 14:360-372.

You et al. (1996), "Behavioral analysis of anisotropic diffusion in image processing," *IEEE Transactions on Image Processing*, 5(11):1539-1553.

Zahm et al. (1998), "Colposcopic appearance of cervical intraepithelial neoplasia is age dependent," *Am. J. Obstet. Gynecol.*, 179(5):1298-1304.

Zeger et al. (1992), "Globally optimal vector quantizer design by stochastic relaxation," *IEEE Transactions on Signal Processing*, 40(2):310-322.

Zeng et al. (1993), "A computerized autofluorescence and diffuse reflectance spectroanalyser system for in vivo skin studies," *Phys. Med. Biol.*, 38:231-240.

Zeng et al. (1997), "Optimization of fast block motion estimation algorithms," *IEEE Transactions on Circuits and Systems for Video Technology*, 7(6):833-844.

Zhang et al. (1999), "Shape from shading: a survey," *IEEE Transactions on Pattern Analysis and Machine Intelligence*, 21(8):690-706.

Zheng et al. (1991), "Estimation of illumination direction, albedo, and shape from shading," *IEEE Transactions on Pattern Analysis and Machine Intelligence*, 13(7):680-702.

Zhengfang et al. (1998), "Identification of Colonic Dysplasia and Neoplasia by Diffuse Reflectance Spectroscopy and Pattern Recognition Techniques," *Applied Spectroscopy*, 52(6):833-839.

\* cited by examiner

FLUORESCENT FIBEROPTIC PROBE FOR TISSUE HEALTH DISCRIMINATION

This application is a continuation of U.S. patent application Ser. No. 10/192,836, filed Jul. 10, 2002, and issued as U.S. Pat. No. 6,768,918 on Jul. 27, 2004 which is incorporated by reference herein in its entirety.

GOVERNMENT RIGHTS

This invention was made with government support under a Small Business Innovation Research Grant (Contract # 1R43CA75773-01) awarded by the Department of Health and Human Services. The government may have certain rights in the invention.

FIELD OF THE INVENTION

This invention relates generally to diagnosis of disease. More particularly, the invention relates to in vivo diagnosis by optical methods.

BACKGROUND OF THE INVENTION

Colonic polyps appear as two major types, neoplastic and non-neoplastic. Non-neoplastic polyps are benign with no direct malignant potential and do not necessarily need to be resected. Hyperplastic polyps, juvenile polyps, mucosal prolapse and normal mucosal polyps are examples of non-neoplastic polyps. Conversely, neoplastic polyps are pre-malignant, a condition requiring resection and further surveillance. Examples of premalignant neoplastic polyps are tubular adenoma, villous adenoma and tubulovillous adenoma.

Conventional laser-induced fluorescence emission and reflectance spectroscopy can distinguish between neoplastic and non-neoplastic tissue with accuracies approaching about 85%. However, typically these methods require that the full spectrum be measured with algorithms dependent on many emission wavelengths.

SUMMARY OF THE INVENTION

The invention provides in vivo diagnostic methods based upon the normalized intensity of light emitted from tissue. In particular, it is an observation of the invention that relevant diagnostic information is provided by comparing the intensities of light emitted from a tissue at two different wavelengths, both normalized over the intensity of light emitted from the same tissue at about 431 nm.

Thus, according to the invention, a comparison of the intensities of two different wavelengths normalized using the intensity at about 431 nm provides diagnostic insight. Preferred methods of the invention comprise obtaining a fluorescent emission having a first intensity at a first wavelength and a second intensity at a wavelength; normalizing the first and second intensities with respect to an intensity at a wavelength of about 431 nm to produce first and second normalized intensities; and determining a state of health of the tissue based upon a comparison of the first and second normalized intensities.

In one embodiment, methods of the invention comprise determining the state of health of the tissue using a classifier function in which the first and second normalized intensities are inputs. In one embodiment, the classifier function is a discrimination function, preferably a linear discrimination function. In other embodiments, the discrimination function is a non-linear discrimination function.

The invention can be applied to analyze a broad range of tissues. Preferably, the tissue to be analyzed is a tissue comprising epithelial cells. In one embodiment, the tissue is selected from the group consisting of cervical tissue, colonic tissue, esophogeal tissue, bladder tissue, and bronchial tissue.

Classifying or comparing normalized intensities into one or more groups may be performed by any acceptable means. There are numerous acceptable approaches to such classifications. For example, one general method of grouping the two normalized intensities is a Bayesian-based classifier using Mahalanobis distances. The Mahalanobis distance is well-known in statistical analysis, and is used to measure a distance between data in a multidimensional space based on characteristics that represent a degree of relationship among the data. Bayesian probabilities have been known in statistical analysis for many years. Specific Bayesian Mahalanobis-based classifier can be selected from linear discriminant analysis, quadratic discriminant analysis, and regularized discriminant analysis. As those familiar with statistical analysis will recognize, linear discrimination analysis and quadratic discriminant analysis are methods that are computationally efficient. Regularized discriminant analysis uses a biasing method based on two parameters to estimate class covariance matrices.

Other ways of comparing the normalized intensities include a binary tree classifier, and an unsupervised learning cluster classifier. Unsupervised learning is characterized by the absence of explicit examples showing what an input/output relation should be. Examples of an unsupervised learning cluster classifier include hierarchical clustering analysis, principal component analysis, fuzzy c-means analysis, and fuzzy k-means analysis. Each of the forgoing analytical techniques is well known in the statistical analysis literature. For example, the fuzzy c-means algorithm divides a data set having an integer number n data points into an integer number c fuzzy clusters, where n>c, while determining a location for each cluster in a multi-dimensional space.

In another aspect, the invention features systems for determining the state of health of a tissue. Systems of the invention comprise an illumination source for illuminating a tissue; a detector for receiving from the tissue light comprising a first intensity at a first wavelength and a second intensity at a second wavelength; a computational module for normalizing the first and second intensities with respect to received light having an intensity at a wavelength of about 431 nm to produce first and second normalized intensities; and an analysis module for determining a state of health of the tissue based upon a comparison of the first and second normalized intensities.

In a preferred embodiment, a system of the invention comprises an optical fiber as the illumination source. The detector may receive light from the tissue by way of a plurality of optical fibers. In a preferred embodiment, at least one of the optical fibers of the system is placed directly in contact with tissue. Preferably, the light received from the tissue is fluorescent light. The analysis module of a system of the invention may comprise a Bayesian Mahalanobis-based classifier function. The Bayesian Mahalanobis-based classifier may be selected from the group consisting of linear discriminant analysis, quadratic discriminant analysis, and regularized discriminant analysis. The analysis module may also comprise a binary tree classifier function or an unsupervised learning cluster classifier. In some embodiments, the unsupervised learning cluster classifier is selected from the group consisting of hierarchical clustering analysis, principal component analysis, fuzzy c-means analysis, and fuzzy k-means analysis.

Systems and methods of the invention are useful in examining a tissue comprising epithelial cells. A method of the invention comprises laser-induced fluorescence using light around 337 nm and a threshold classification model that depends on two fluorescence intensity ratios normalized by the intensity of fluorescence at about 431 nm.

The invention enables determining whether a polyp is neoplastic. Systems and methods of the invention enable such determination at the time of endoscopy particularly for diminutive polyps. In a preferred embodiment, the invention provides for identification of polyps (or other features) under about 10 mm in size. In a further preferred embodiment, the invention provides for identification of polyps (or other features) under about 10 mm in size in real time.

The combination of a new design of a fiberoptic probe for making measurements, an analytic method based on a small number of data points, and a simple method of obtaining a normalization factor for the data used provides enhanced diagnostic accuracy in distinguishing between neoplastic and non-neoplastic polyps.

The invention provides methods that reliably distinguish between neoplastic and non-neoplastic tissue at the time of endoscopy, colonoscopy, colposcopy, or other similar examinations. As a result, patients with non-neoplastic lesions are not subjected to the risk, discomfort and expense of biopsies or excisions. Patients with neoplastic lesions can be identified immediately and treated.

The foregoing and other objects, aspects, features, and advantages of the invention will become more apparent from the following description and from the claims.

BRIEF DESCRIPTION OF THE DRAWINGS

The objects and features of the invention can be better understood with reference to the drawings described below. The drawings are not necessarily to scale, emphasis instead generally being placed upon illustrating the principles of the invention. In the drawings, like numerals are used to indicate like parts throughout the various views.

DETAILED DESCRIPTION

Figure 1:
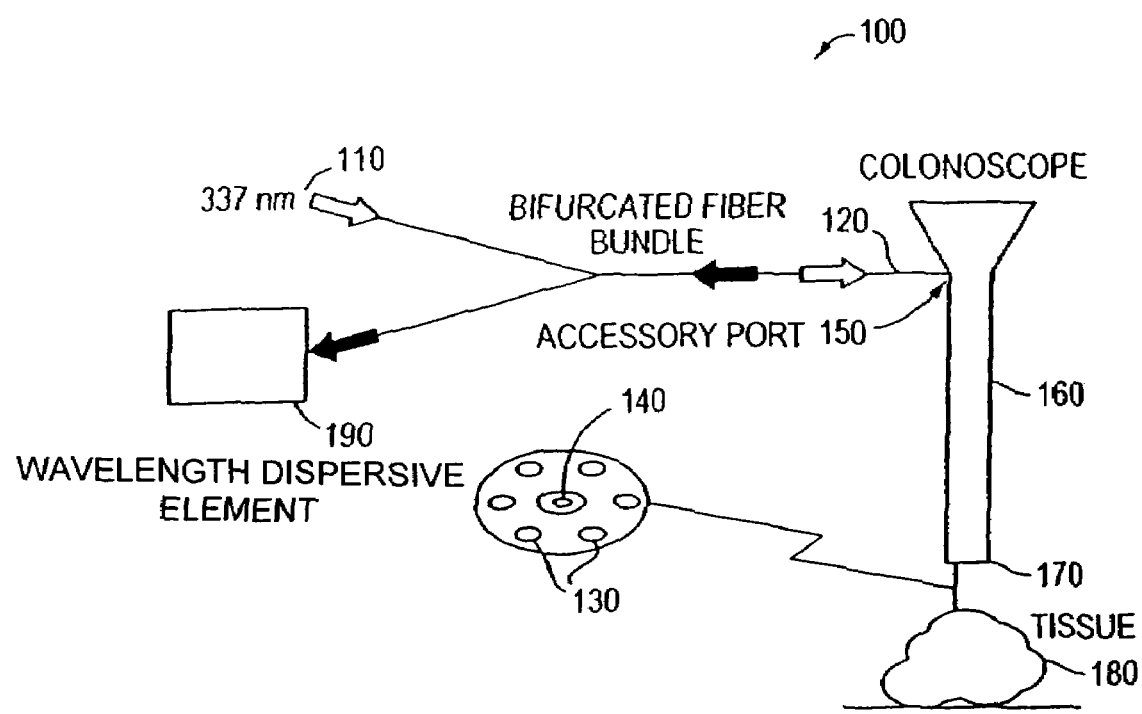
FIG. 1 is a schematic diagram showing an embodiment of the apparatus according to principles of the invention.

In one aspect, the invention utilizes the intensity of fluorescence observed at an isosbestic-like point as a point for normalization. An isosbestic point is a point in wavelength space (or its equivalent) at which a multi-component system exhibits a constant absorbance independent of the relative proportions of the components. Following normalization to peak fluorescence intensity, polyp fluorescence spectra exhibits nearly constant fluorescence intensities at 431 nm. A preferred isosbestic-like point for use in methods of the invention is 431 nm.

According to the invention, normalizing polyp fluorescence spectra to an isosbestic point is nearly equivalent to normalizing to their peak intensities. Generally, the invention involves illuminating a specimen and observing the intensity of responsive light at each of first and second wavelengths. These intensities are normalized with respect to the intensity of light at an isosbestic point. Normalized intensities are typically obtained by dividing an intensity of responsive light at a wavelength by the intensity of light at the isosbestic wavelength. In a preferred embodiment, the fluorescence isosbestic point occurs at a wavelength of about 431 nm.

The first and second wavelengths may be conveniently selected in accordance with a discrimination function analysis, which is described below in greater detail. The normalized responses are used at input values for the discrimination function analysis. The output of the discrimination function analysis is an indication that the specimen examined is healthy or is diseased.

The discrimination analysis can be linear or nonlinear. In general terms, the discrimination function is a mathematical relationship that is constructed in at least two-dimensional space. The mathematical relationship is constructed in relation to groupings of observations corresponding to one or more known medical conditions as compared to observations corresponding to another known condition (e.g., healthy). The discrimination function used in methods of the invention is a mathematical representation of one or more boundaries that separate observations obtained from the sample being interrogated from those corresponding to one or more groups associated with a known condition. As is appreciated by the skilled artisan, numerous discrimination techniques are available for application of the invention. Numerous such techniques are discussed below.

EXAMPLE 1

In one embodiment, the invention is practiced by illuminating tissue with 337 nm excitation light delivered via a single optical fiber. Light that is remitted is collected with a plurality of optical fibers surrounding the illumination fiber. In one embodiment, signals from the individual collection fibers can be averaged into a single spectrum thereby increasing sensitivity. In an alternative embodiment, the signals from the individual collection fibers can be analyzed as discrete signals, for example, by comparing the different signal to determine an extent of tissue that provides a particular response.

An exemplary apparatus 100 used in this embodiment of the invention is shown in FIG. 1. The apparatus 100 includes a source 110 of 337 nm illumination as the excitation source. The excitation illumination is introduced into an optical fiber 120 for delivery to the tissue under examination. The illumination fiber 120 can be tapered starting at about 0.4 mm in diameter at the proximal end and ending at about 0.1 mm at its distal end. In one embodiment, a plurality of optical fibers 130 are used to collect the response signal from the tissue under examination. In the embodiment shown, six collection fibers 130 are placed in a hexagonal array about the central optical fiber 120 that carries the excitation illumination. This geometry is termed herein the "six-around-one fiberoptic probe." In alternative embodiments, additional hexagonal layers of fibers disposed so as to surround the collection fibers 130. The collection fibers are about 0.1 mm in diameter. The fiberoptic catheter 140 is delivered through the accessory port 150 of a typical endoscope 160 with the distal tip 170 gently touching tissue 180 to be examined. In one embodiment, the returned light is separated into fluorescence bands at 403, 414 and 431 nm using a wavelength dispersive element 190 such as a spectrograph or dichroic filter system. The width of the bands should preferably be under 5 nm. Two intensity ratios ($I_{403}/I_{431}$ and $I_{414}/I_{431}$) are then formed and used as input values in a linear discriminant analysis (LDA) threshold model to produce a score indicative of the health of the tissue. Treatment or further diagnostic procedures are based on a characteristic of the score, such as its sign.

This invention, in one embodiment, relates to an optical probe and methods for identifying neoplastic tissues of the colon during endoscopy or colonoscopy and of the cervix of the uterus during colposcopy as well as cancerous and/or pre-cancerous lesions of other organs, such as the esophagus, the urinary bladder, the oral cavity, and the bronchotracheal tree. Systems and methods of the invention can be usefully employed in examining a tissue comprising epithelial cells. A probe according to the invention comprises a plurality of collection fibers surrounding a single illumination fiber. Preferably, the plurality of collection fibers is six fibers. In a preferred embodiment, at least one of the optical fibers of the probe is placed directly in contact with tissue. A method of the invention comprises laser induced fluorescence using 337 nm excitation and a threshold classification model that depends on two fluorescence intensity ratios normalized by the intensity of fluorescence at about 431 nm. In a preferred embodiment, the intensity at about 403 nm is divided by the intensity at about 431 nm and the intensity at about 414 nm is divided by the intensity at 431 nm.

The invention enables determining whether a polyp is neoplastic. Systems and methods of the invention enable such determination at the time of endoscopy particularly for diminutive polyps. In an exemplary embodiment, fluorescent intensity at frequencies other than about 403 nm and about 414 nm are observed, and are normalized by dividing by the intensity of fluorescence observed at about 431 nm.

In a preferred embodiment, the invention provides for identification of polyps (or other features) under about 10 mm in size. In a further preferred embodiment, the invention provides for identification of polyps (or other features) under about 10 mm in size in real time.

Figure 2:
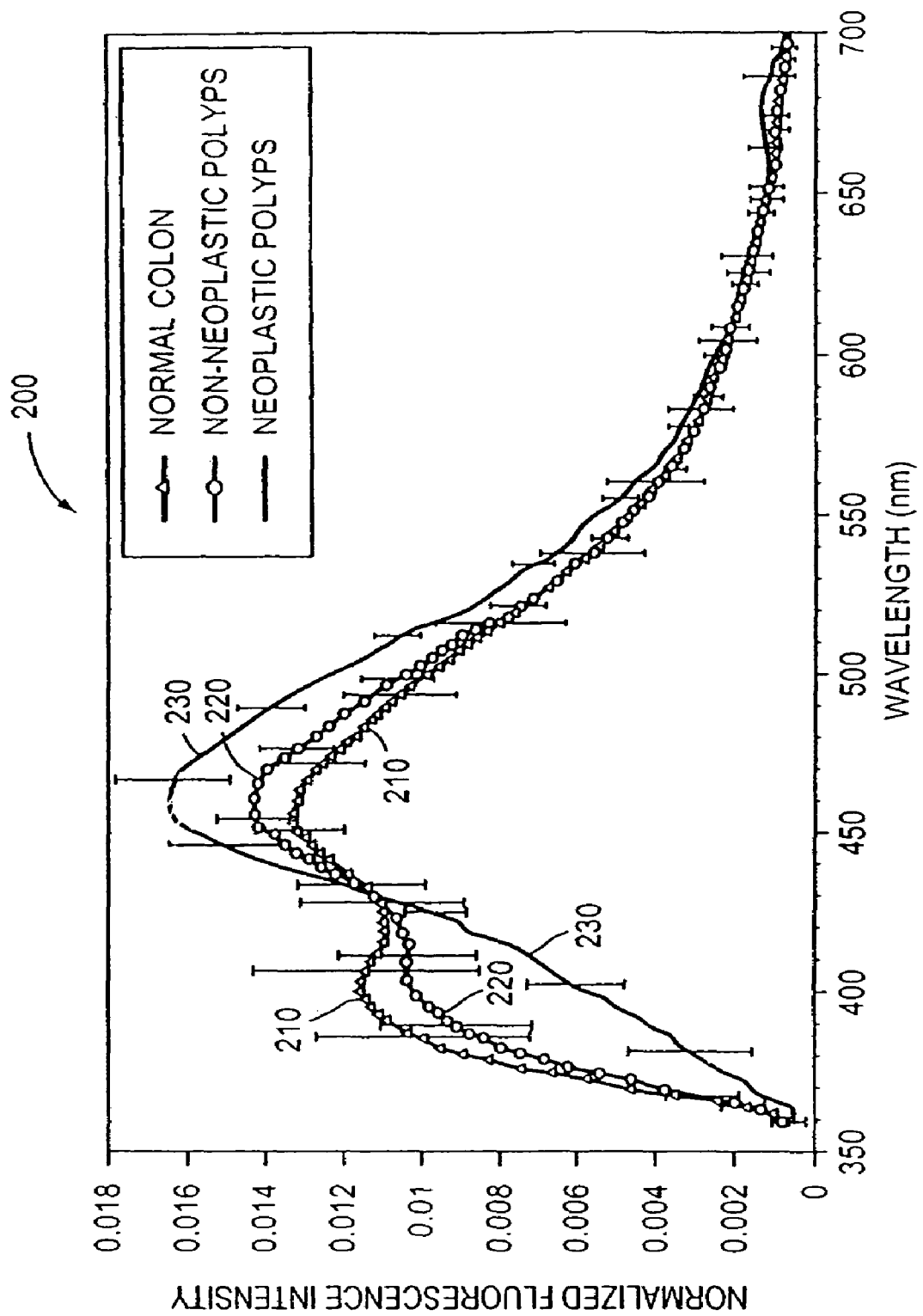
FIG. 2 is a plot of the normalized fluorescence spectra of normal colon, neoplastic polyps and non-neoplastic polyps showing a quasi-isosbestic point at 431 nm, according to an embodiment of the invention.

Referring to FIG. 2, a plot 200 depicting a plurality of response spectra is shown, for different tissue types illuminated with the same 337 nm excitation-light. In the example shown, the spectra observed correspond to tissues including normal colon 210, non-neoplastic polyps 220, and neoplastic polyps 230. There is a quasi-isosbestic point at 431 mm. The spectra 210, 220, 230 shown in FIG. 2 were recorded with the six-around-one fiberoptic probe.

Changes in optical properties of collagen and blood are the predominant factors in diagnostic differentiation among normal tissue, non-neoplastic polyps, and neoplastic polyps. An algorithm that treats collagen fluorescence, having a peak at about 403 nm in the system of the invention, and hemoglobin absorption, having a peak at about 414 nm for oxyhemoglobin, is sensitive to these changes.

Collagen and blood reside underneath the superficial cellular layer. A fiberoptic geometry designed to probe deeper into tissue but not too deep is more sensitive to changes in collagen and blood and hence in differentiating between types of polyps. The six-around-one fiberoptic probe used according to principles of the invention probes deeper into tissue than does a single fiber system.

Interpatient variability in the intensity of fluorescent response is typically large and affects the diagnostic accuracy of techniques based on absolute fluorescence intensities. Historically, effective diagnostic algorithms have used some form of normalization to reduce interpatient variability. One common approach that has been used is to preprocess the data by normalizing the area under each fluorescence spectrum to unity. However, this approach requires that the entire fluorescence spectrum be measured to calculate the area to be used for the normalization factor. The necessity to record an entire spectral response simply to be able to obtain normalization data is redundant and inefficient. The inefficiency is particularly acute if only the emissions at 1 or 2 wavelengths are to be analyzed.

According to the invention, a quasi-isosbestic point exists at about 431 nm between the fluorescence spectra of normal tissue, hyperplastic polyps and adenomatous polyps. The quasi-isosbestic point is used as a normalization factor that provides effective normalization while requiring fluorescence to be measured at only one addition emission wavelength. For other types of pre-cancerous and/or cancerous polyps, other chemical substances are involved in the progress of the disease. These chemical substances provide characteristic signals that can occur at wavelengths other than at about 403 nm and about 414 nm.

The combination of a new design of a fiberoptic probe for making measurements, an analytic method based on a small number of data points, and a simple method of obtaining a normalization factor for the data used provides enhanced diagnostic accuracy in distinguishing between neoplastic and non-neoplastic polyps. The efficacy of the new system and method is demonstrated in a single-center prospective clinical trial. A higher fraction of polyps were correctly classified with this technique, (e.g., accuracy=86%) when compared to other approaches. The accuracy of the method using two emission wavelengths is better than that obtained in retrospective clinical trials requiring many more wavelengths. A retrospective trial is one in which one determines the sensitivity of an algorithm that was retrospectively optimized with data in hand. A prospective trial is one that uses a retrospectively trained algorithm in a prospective analysis of data collected after the algorithm is defined and tested.

Analysis Method

Figure 3:
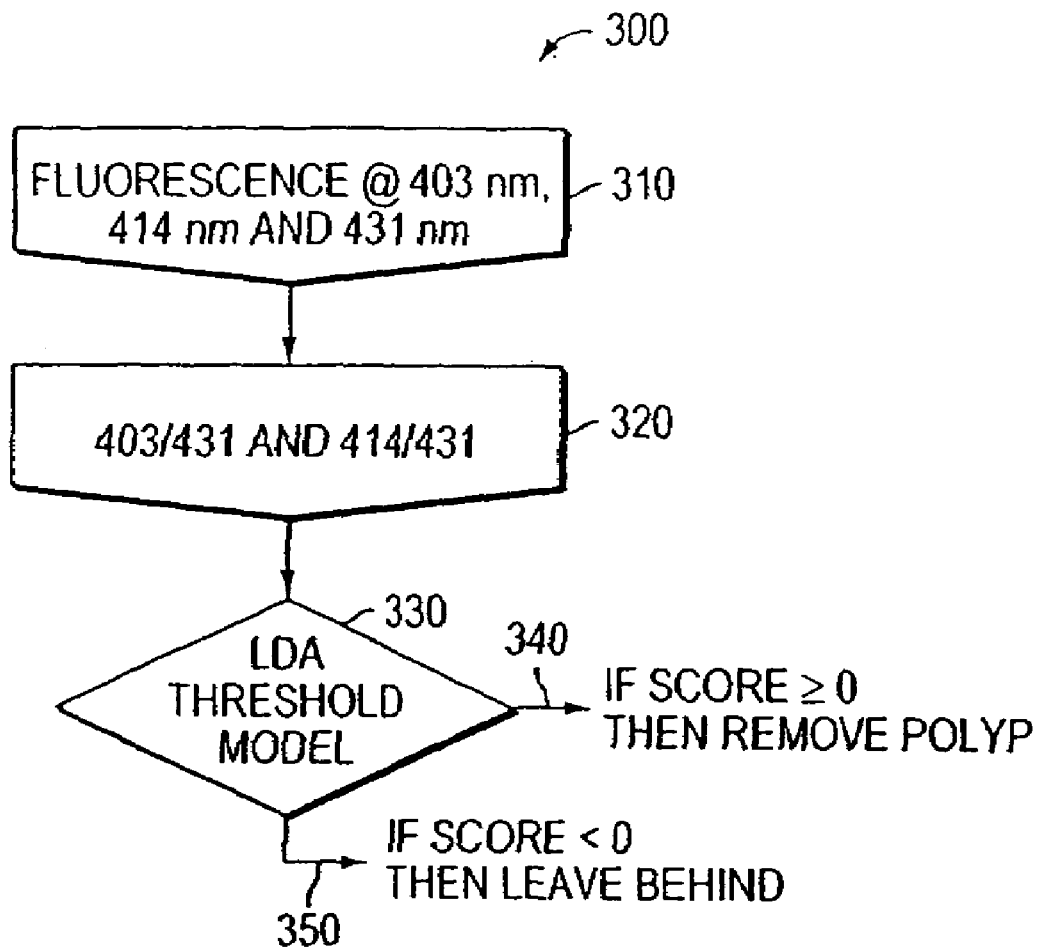
FIG. 3 is a flow diagram showing the steps of the analytical method according to principles of the invention.

FIG. 3 is a flow diagram 300 showing the steps of an illustrative analytical method as applied to the optical signals observed from colonic polyps. The method involves, in the example provided above, observing fluorescent intensities at about 403, about 414 and about 431 mm, as shown at step 310. The ratio of the intensity at about 403 mm to that at about 431 nm ($I_{403}/I_{431}$), and the ratio of the intensity at about 414 nm to that at about 431 nm ($I_{414}/I_{431}$) are formed, as indicated at step 320. The two ratios are then examined by comparison to a linear discrimination function, using linear discrimination analysis (LDA), as shown at step 330. A score value greater than zero is indicative of neoplasia, while a score value less than zero indicates non-neoplasia. Resection can be performed, or omitted, based on the score value that is obtained. Result 340 represents performing resection, while result 350 represents not performing resection.

Sensitivity Analysis

Figure 4:
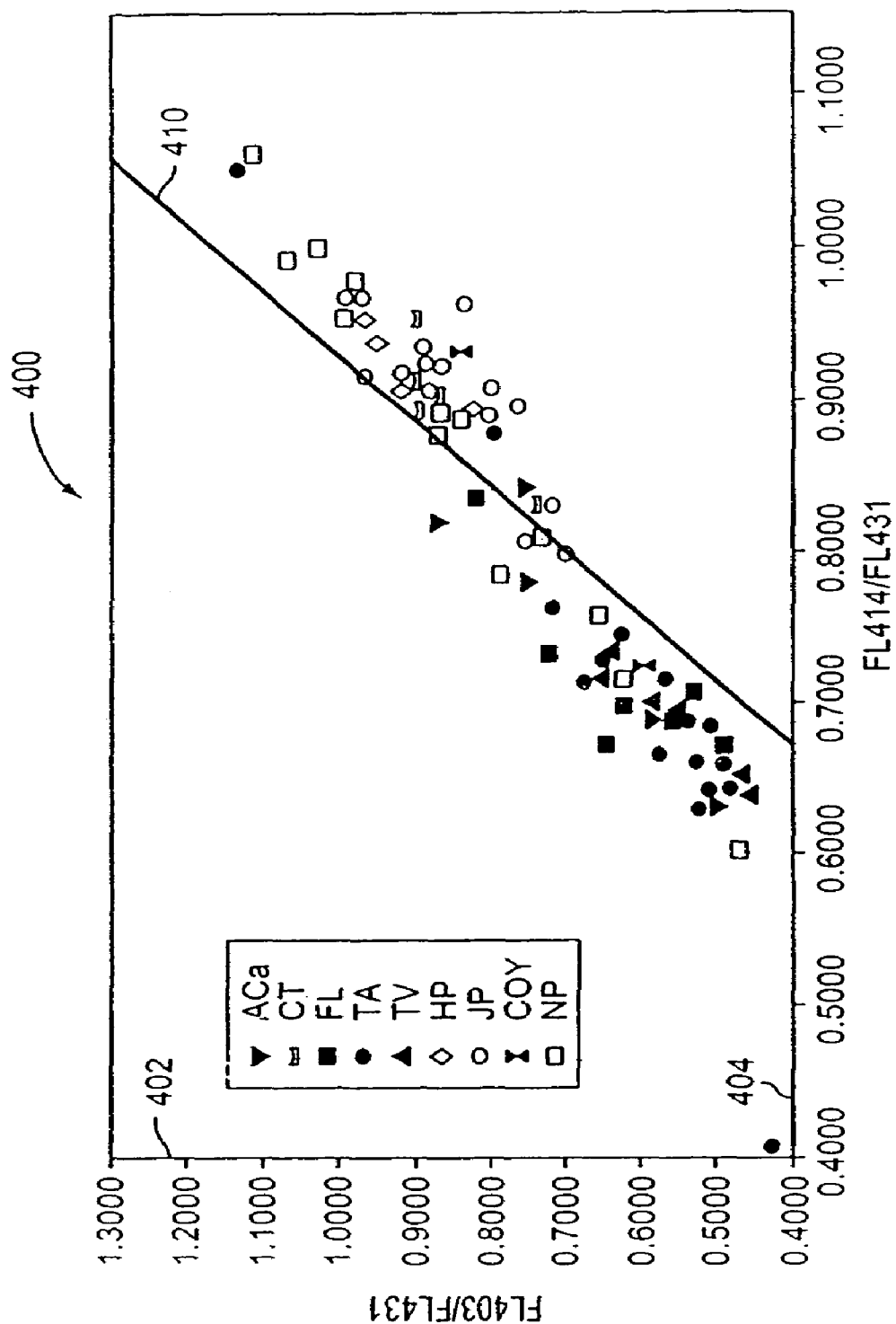
FIG. 4 is a graph showing polyp classification results obtained using a linear discriminant analysis according to principles of the invention.

FIG. 4 is a graph 400 showing illustrative polyp classification results obtained using a linear discriminant analysis for the colonic polyp example discussed above. One hundred and fifty patients were enrolled in a prospective study in which 94 polyps were collected from 50 patients. In FIG. 4, the about 403 nm to about 431 mm fluorescence intensity ratio ($I_{403}/I_{431}$) was plotted along the vertical axis 402 against the about 414 mm to about 431 mm ratio ($I_{414}/I_{431}$)

plotted along the horizontal axis 404 for a given polyp. The LDA threshold discrimination model is depicted as the line 410 in FIG. 4 where polyps corresponding to data points that lie above the line 410 are classified as neoplastic polyps and polyps corresponding to data points that lie below the line 410 are classified as non-neoplastic polyps. Using this model, 47 of 52 neoplastic polyps and 34 of 42 non-neoplastic polyps were classified correctly resulting in a sensitivity and specificity of 90% and 81%, respectively. In addition, 80 of 86 normal colonic tissue sites and 3 of 3 frank adenocarcinomas were correctly classified.

OTHER EXAMPLES

The apparatus of FIG. 1 is used in other exemplary systems and methods of the invention. Specimens to be tested for diagnostic purposes are illuminated with excitation radiation, such as 337 nm illumination. Intensities of fluorescent responses at first and second wavelengths are observed, and are normalized using an intensity of a response at an isosbestic point. In preferred embodiments, the isosbestic point occurs at 431 nm. The normalized intensities are analyzed by comparison to a discrimination function.

Various linear or non-linear discriminant functions can be devised using the complex relationship between tissue fluorescence measured on the surface and the distribution of different fluorophores that exist in different tissue layers. The analysis is further complicated by primary absorption of the excitation light and secondary absorption of the emitted light at different wavelengths by the same fluorophores and other chromophores as the light used for excitation and the emitted light propagate through scattering media such as tissue. Diagnostic systems and methods of the invention will operate according to a non-linear discriminant when an excess and/or a deficit of one or more of such substances is indicative of a condition of health.

Diagnostic systems and methods of the invention will operate according to a non-linear discriminant based on other factors as well. For example, in the field of colposcopy, nonlinear discriminants can vary with other factors such as the age or race of the patient or whether the patient is pre-, peri- or post-menopausal.

Potential Cost Savings

The ability to identify and distinguish benign and malignant polyps in situ could result in substantial cost savings. In this particular example, 39 of 94 polyps would have been spared from being resected and biopsied, representing a 41% savings in surgical and pathology charges. However, at present there is a false negative rate of 9.6%. The long term outcome of not resecting these polyps will need to be determined. In comparison, other techniques spared 14% of the polyps from being biopsied and had a false negative rate of 0.9%. If polyps greater than 5 mm in the latter study are excluded from this analysis then 27% of the polyps would not have been biopsied and the technique would have a 3.2% false negative rate.

Application to Other Tissues

The systems and methods of the invention have been described with regard to observations on colonic tissue. The invention, involving a new probe design and analytical method, can enhance the accuracy for identifying neoplasia in other tissues such as the cervix of the uterus, the esophagus, the urinary bladder, the oral cavity, and the bronchotracheal tree.

Equivalents

While the invention has been particularly shown and described with reference to specific preferred embodiments, it should be understood by those skilled in the art that various changes in form and detail may be made therein without departing from the spirit and scope of the invention.

What is claimed is:

1. A system for determining a condition of a tissue, the system comprising:
    an illumination source for illuminating a tissue with light at an excitation wavelength;
    a detector for determining a first and second intensity of received electromagnetic radiation from said tissue upon illumination at said excitation wavelength, wherein said first intensity corresponds to a first wavelength and said second intensity corresponds to a second wavelength different from said first wavelength;
    a computational module for normalizing said first and second intensities with an intensity corresponding to an isosbestic point, and for determining a condition of said tissue based at least in part on said normalized first and second intensities.

2. The system of claim 1, wherein said excitation wavelength is 337 nm.

3. The system of claim 1, wherein said isosbestic point is a wavelength of about 431 nm.

4. The system of claim 1, wherein said illumination source comprises an optical fiber.

5. The system of claim 1, wherein said detector receives light from said tissue by way of a plurality of optical fibers.

6. The system of claim 5, wherein said detector receives fluorescent light from said tissue by way of said plurality of optical fibers.

7. The system of claim 1, wherein said computational module comprises a Bayesian Mahalanobis-based classifier function.

8. The system of claim 7, wherein said Bayesian Mahalanobis-based classifier is selected from the group consisting of linear discriminant analysis, quadratic discriminant analysis, and regularized discriminant analysis.

9. The system of claim 1, wherein said computational module comprises a binary tree classifier function.

10. The system of claim 1, wherein said computational module comprises an unsupervised learning cluster classifier.

11. The system of claim 10, wherein said unsupervised learning cluster classifier is selected from the group consisting of hierarchical clustering analysis, principal component analysis, fuzzy c-means analysis, and fuzzy k-means analysis.

* * * * *